United States Patent [19]

Krimm et al.

[11] Patent Number: 4,501,905
[45] Date of Patent: Feb. 26, 1985

[54] CYCLIC CARBONIC ACID DERIVATIVES

[75] Inventors: Heinrich Krimm; Hans-Josef Buysch, both of Krefeld, Fed. Rep. of Germany

[73] Assignee: Bayer Aktiengesellschaft, Leverkusen, Fed. Rep. of Germany

[21] Appl. No.: 555,754

[22] Filed: Nov. 28, 1983

Related U.S. Application Data

[62] Division of Ser. No. 340,943, Jan. 20, 1982, Pat. No. 4,440,937.

[30] Foreign Application Priority Data

Jan. 30, 1981 [DE] Fed. Rep. of Germany ....... 3103139
Jan. 30, 1981 [DE] Fed. Rep. of Germany ....... 3103138
Jan. 30, 1981 [DE] Fed. Rep. of Germany ....... 3103136

[51] Int. Cl.³ .......................................... C07D 319/06
[52] U.S. Cl. .................................................. 549/228
[58] Field of Search ........................................ 549/228

[56] References Cited

U.S. PATENT DOCUMENTS 3,532,715  10/1970  Hostettler et al. ............... 260/340.2

FOREIGN PATENT DOCUMENTS 950850  10/1956  Fed. Rep. of Germany .
972209   6/1959  Fed. Rep. of Germany .
972508   8/1959  Fed. Rep. of Germany .
787406  12/1957  United Kingdom ................ 549/228

Primary Examiner—Norma S. Milestone
Attorney, Agent, or Firm—Sprung Horn Kramer & Woods

[57] ABSTRACT

New cyclic carbonic acid derivatives of the formula

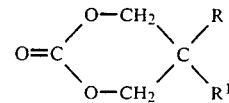

in which
R denotes either —CH$_2$OH, R$^1$ then representing an alkyl radical having 1 to 4 C atoms, or

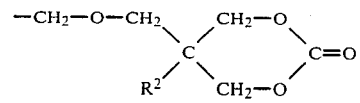

R$^1$ and R$^2$ then independently of one another representing methyl or ethyl, or

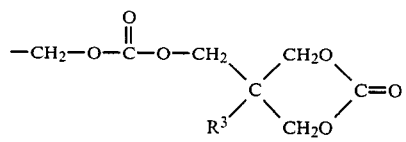

R$^1$ and R$^3$ then each representing an alkyl radical having 1 to 4 C atoms,
or in which
R and R$^1$ together denote

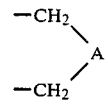

wherein
A represents the group

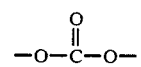

or oxygen, a process for their preparation, and their use as copolymerization components in the preparation of polycarbonates.

2 Claims, No Drawings

CYCLIC CARBONIC ACID DERIVATIVES

This is a division of application Ser. No. 340,943, filed Jan. 20, 1982, now U.S. Pat. No. 4,440,937, issued Apr. 3, 1984.

The present invention relates to new cyclic carbonic acid derivatives of the formula (I)

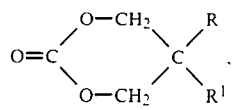

in which
R denotes either —CH$_2$OH, R$^1$ then representing an alkyl radical having 1 to 4 C atoms, or

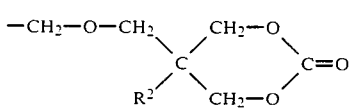

R$^1$ and R$^2$ then independently of one another representing methyl or ethyl, or

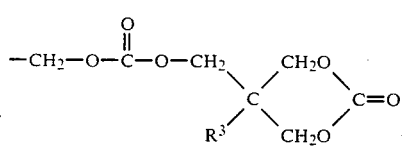

R$^1$ and R$^3$ then each representing an alkyl radical having 1 to 4 C atoms,
or in which
R and R$^1$ together denote

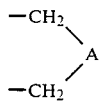

wherein
A represents the group

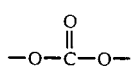

or oxygen.

The most important of the new carbonic acid derivatives are the following:

(a) 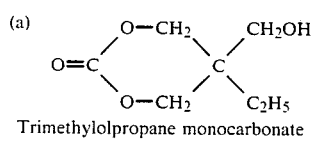
Trimethylolpropane monocarbonate (b) 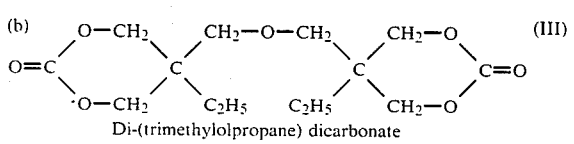
Di-(trimethylolpropane) dicarbonate (c) 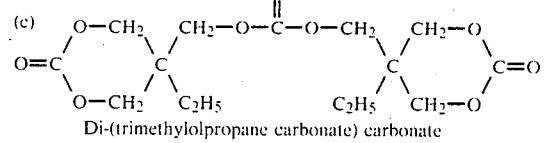
Di-(trimethylolpropane carbonate) carbonate (d) 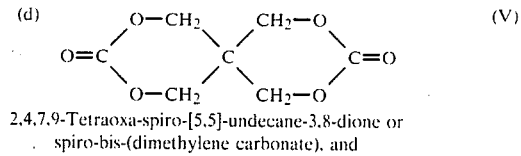
2,4,7,9-Tetraoxa-spiro-[5.5]-undecane-3,8-dione or spiro-bis-(dimethylene carbonate), and (e) 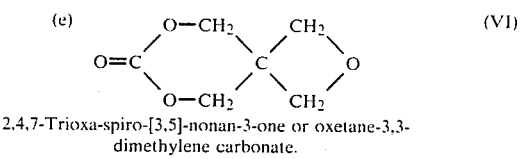
2,4,7-Trioxa-spiro-[3.5]-nonan-3-one or oxetane-3,3-dimethylene carbonate.

The present invention furthermore relates to a process for the preparation of the new cyclic carbonic acid derivatives of the formula (I)

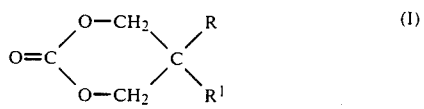

in which
R denotes either —CH$_2$OH, R$^1$ then representing an alkyl radical having 1 to 4 C atoms, or

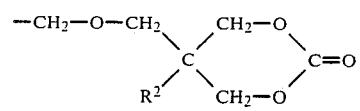

R$^1$ and R$^2$ then independently of one another representing methyl or ethyl, or

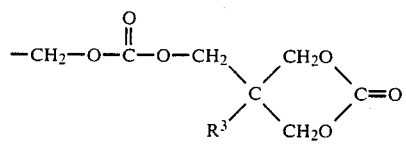

R$^1$ and R$^3$ then each representing an alkyl radical having 1 to 4 C atoms,
or in which
R and R$^1$ together denote

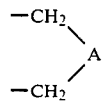

wherein
A represents the group

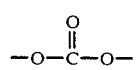

or oxygen, which comprises contacting a polyol of the formula (VII)

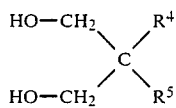

in which
R$^4$ denotes either —CH$_2$OH, R$^5$ then representing an alkyl radical having 1 to 4 C atoms or —CH$_2$OH or R$^4$ represents

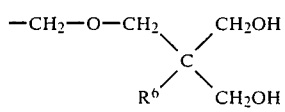

R$^5$ and R$^6$ then independently of one another representing methyl or ethyl,
with a carbonic acid derivative from the group comprising phosgene, a chlorocarbonate, a dialkyl carbonate and a diaryl carbonate to give a soluble polycarbonate. In those cases in which R$^4$ represents —CH$_2$OH and R$^5$ represents an alkyl radical having 1 to 4 C atoms, or R$^4$ represents the radical

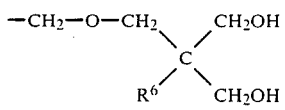

the catalyst used in the reaction to give a soluble polycarbonate should be removed, and in those cases in which R$^4$ represents —CH$_2$OH and R$^5$ represents —CH$_2$OH this catalyst is optionally removed. If desired, the soluble polycarbonate is thereafter converted, at elevated temperature and under reduced pressure, into a crosslinked insoluble polycarbonate. This latter polycarbonate, whether soluble or insoluble, can be polymerized at elevated temperature and under reduced pressure, and the new carbonic acid derivatives of the formula (I), which are formed in the process, can then be separated off.

In the preparation of new carbonic acid derivatives of the formula (I) wherein R=—CH$_2$OH and R$^1$=C$_1$- to C$_4$-alkyl, the procedure is preferably carried out as follows: a soluble polycarbonate is prepared from a trimethylolalkane of the formula (VIII)

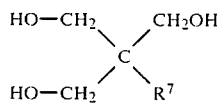

wherein R$^7$=C$_1$- to C$_4$-alkyl,
and an equimolar quantity of a carbonic acid derivative from the group comprising phosgene, chlorocarbonates, dialkyl carbonates and diaryl carbonates, with the addition of strongly basic catalysts, the catalysts used, the by-products thereof and/or other extraneous compounds are removed, the soluble polycarbonate thus pre-treated is heated to temperatures which are adequate for depolymerization and the carbonic acid derivatives which are formed in the process and are of the formula (I) wherein R=—CH$_2$OH and R$^1$=C$_1$- to C$_4$-alkyl are separated off.

In this process, trimethylolethane or trimethylolpropane is preferably employed as the trimethylolalkane, that is to say R$^7$ is preferably methyl or ethyl in formula (VIII). The strongly basic catalysts can, for example, be sodium or potassium hydroxide, carbonate or phenolate. The removal of the catalysts, the by-products thereof and/or other extraneous compounds can be effected in various ways.

For this purpose, the polycarbonate is preferably first dissolved in a suitable solvent, for example in methylene chloride, methylene chloride and dioxane, or toluene. The resulting polycarbonate solution can then be washed, for example with water, in particular with distilled or demineralized water, for example from 2 to 5 times.

In this process, the polycarbonate solution is preferably treated, before the washes with water, with a dilute acid, for example with up to 20% by weight of aqueous hydrochloric acid or sulphuric acid. The removal of the catalysts used for the preparation of the polycarbonates, the by-products of these catalysts and/or other extraneous compounds present can also be carried out by treating the polycarbonate solution with an ion exchanger, solutions of the polycarbonate in water-miscible solvents, such as acetone or dioxane, also being suitable for this purpose. Acid-activated bleaching earths and/or sulphonated crosslinked polystyrenes are preferably employed for this purpose. In general, it is advantageous to remove as completely as possible, before the depolymerization, the auxiliaries (for example water, solvents, acids and/or ion exchangers) used for the removal of the catalysts employed in the preparation of the polycarbonates, the by-products of these catalysts and/or other extraneous compounds.

The depolymerization of the polycarbonate thus pre-treated is then effected by heating. For this purpose, temperatures in the range of from 150° to 240° C. are generally necessary. The depolymerization is preferably carried out at temperatures in the range of from 160° to 220° C.

The cyclic carbonates which are formed during the depolymerization and are of the formula (I) wherein R=—CH$_2$OH and R$^1$=C$_1$- to C$_4$-alkyl are preferably removed at the rate at which they are formed. This can be effected, for example, by carrying out the depolymerization in vacuo. For this process, the vacuum is advantageously chosen such that the cyclic carbonates formed distil off and can be collected, after cooling, in a receiver. Depending on the volatility of the cyclic carbonates formed, the pressures used can, for example, be in the range of from 0.001 to 25 mbars. However, the cyclic carbonates formed can also be removed, for example, by passing an inert gas, under pressures of, for example, from 0.001 to 25 mbars, through the vessel in which the depolymerization takes place, and separating off, from the gas stream leaving the depolymerization vessel, the cyclic carbonates formed. Examples of suitable inert gases for this purpose are nitrogen, carbon dioxide or noble gases.

The cyclic carbonates of the formula (I) wherein R=—CH$_2$OH and R$^1$=C$_1$- to C$_4$-alkyl pass over, in this depolymerization, at a constant temperature and without perceptible decomposition (decarboxylation), and, after cooling, can be isolated as crystalline monomers, in good yields. The polycarbonates to be depolymerized tend to gelatinize during the depolymerization, but can be almost completely depolymerized, without difficulties, even in this state.

In many cases, the cyclic carbonates produced in the depolymerization and of the formula (I) wherein R=—CH$_2$OH and R$^1$=C$_1$- to C$_4$-alkyl are already sufficiently pure for further uses. However, they can be further purified if desired. This purification can be effected, for example, by recrystallization from a suitable solvent (for example ethyl acetate, toluene, cyclohexane, diethyl ether or carbon tetrachloride) or by distillation under reduced pressure.

In the preparation of the new carbonic acid derivatives of the formula (I) wherein R and R$^1$ together are

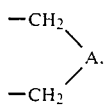

wherein
A represents the group

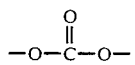

or oxygen,
the process is preferably carried out such that
(a) pentaerythritol is reacted with a carbonic acid derivative from the group comprising phosgene, chlorocarbonates, dialkyl carbonates and diaryl carbonates, optionally in the presence of basic compounds, to give a soluble precursor,
(b) the basic compounds are thereafter removed if appropriate,
(c) a crosslinked polycarbonate is prepared from the soluble precursor by heating the latter to 100° to 250° C., under pressures in the range of from 1 to 140 mbars,
(d) the crosslinked polycarbonate is depolymerized, optionally in the presence of catalysts, at from 200° to 300° C. and under pressures in the range of from 0.001 to 1 mbar, and
(e) the bicyclic carbonic acid derivatives which sublime or distil off in step (d) and are of the formula (I) wherein R and R$^1$ together are

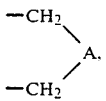

wherein
A represents the group

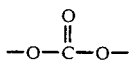

or oxygen,
are collected and, if desired, separated.

The reaction of pentaerythritol to be carried out in step (a) of this process can be effected, in principle, using phosgene, chlorocarbonates, dialkyl carbonates or diaryl carbonates. For ecological reasons, the reaction with dialkyl carbonates or diaryl carbonates is preferred, for which reason essentially this procedure is described below. One skilled in the art experiences no difficulties in carrying out corresponding reactions using phosgene or chlorocarbonates.

The essential point in step (a) is that the reaction leads to a soluble precursor and not to insoluble, strongly crosslinked polymers. This can be achieved, for example, by employing a large excess of dialkyl or diaryl carbonates, for example from 4 to 10 mols of carbonate per mol of pentaerythritol.

The reaction with carbonates is preferably carried out in the presence of transesterification catalysts. The following may be mentioned as examples of such transesterification catalysts: oxides, hydroxides, alcoholates, carboxylates and carbonates of alkali metals, in particular sodium and potassium, and of aluminum, thallium or lead, which can be employed, for example, in quantities of from 0.1 to 2 g per mol of pentaerythritol.

The reaction between carbonates and pentaerythritol can be carried out, for example, by mixing the components, adding one or more transesterification catalysts, heating the mixture, for example to temperatures in the range of from 120° to 140° C., and distilling off the alcohol formed, if desired under reduced pressure and, if desired, over a column. When diethyl carbonate is employed as the carbonate, the reaction mixture can, for example, be boiled under reflux at a temperature of from about 120° to 130° C., and the resulting ethyl alcohol can be separated off over a column, at about 78° to 80° C.

If, instead of carbonates, the reaction is carried out using phosgene or chlorocarbonates, for example phenyl chlorocarbonate, the reaction is preferably carried out in the presence of a solvent, for example ethyl acetate, and an acid-binding agent, for example dimethylaniline, at temperatures of, for example, from 20° to 80° C. in a manner which is in principle known. In this case, after the end of the reaction, the solvent, and the salt formed from the acid-binding agent, have to be removed, for example by washing with water and stripping off the solvent under reduced pressure.

If, in step (a), basic compounds have been employed, for example as transesterification catalysts, these compounds have to be removed in step (b) if the spiro-bis-(dimethylene carbonate) (see formula (V)) is to be prepared. If oxetane-3,3-dimethylene carbonate (see formula (VI)) is to be prepared, such basic compounds can remain in the precursor prepared in step (a) or can be removed.

The removal of the basic compounds can be carried out in various ways. The procedure is preferably carried out as described for the preparation of carbonic acid derivatives of the formula (I) wherein R=—CH$_2$OH and R$^1$=C$_1$- to C$_4$-alkyl.

In general, it is advantageous to remove as completely as possible, before carrying out step (c), the auxiliaries (for example water, acids, solvents and/or ion exchangers) used for the removal of the basic compounds.

In step (c), a crosslinked polycarbonate is then prepared from the soluble precursor, freed, if desired, from basic compounds, by heating the precursor preferably to 100° to 250° C., under pressures in the range of, preferably, from 1 to 140 mbars. This step is particularly preferably carried out at temperatures in the range of from 140° to 210° C. and under pressures in the range of from 5 to 50 mbars. In this step, the pressure and temperature conditions should generally be adjusted within the given limits such that no pentaerythritol derivatives distil off or sublime, but only excess starting material, for example diethyl carbonate, and/or products resulting during the formation of the crosslinked polycarbonate, for example diethyl carbonate, or, in the case in which phenyl chlorocarbonate is employed in step (a), phenol. After step (c) has been carried out, the crosslinked polycarbonate formed remains as a residue.

Under certain circumstances, for example if pentaerythritol is reacted with a dialkyl carbonate in step (a) and basic compounds have been separated off in step (b), and when step (c) is carried out no catalysts are present and very low pressures, for example below 0.1 mbar, are used, one can separate off, by rapid distillation, non-bicyclic pentaerythritol derivatives, such as pentaerythritol monocarbonate bis-alkyl carbonates (see formula (IX)) and pentaerythritol tetrakis-alkyl carbonates (see formula (X)).

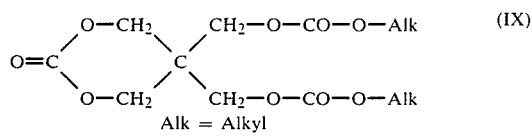

Alk = Alkyl

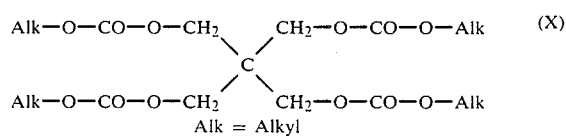

Alk = Alkyl

The compounds of the formula (I) wherein R and R¹ together are

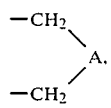

wherein
A represents the group

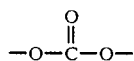

or oxygen,
can be obtained from the compounds which correspond to the formulae (IX) and (X), by subjecting the latter compounds to process steps (c), (d) and (e).

In step (d), the crosslinked polycarbonate is depolymerized at temperatures in the range of, preferably, from 200° to 300° C., particularly preferably from 220° to 280° C., and under pressures in the range of, preferably, from 0.001 to 1 mbar, particularly preferably 0.01 to 0.1 mbar. In this step, the compounds corresponding to the formula (I) wherein R and R¹ together are

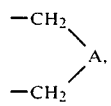

wherein
A represents the group

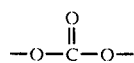

or oxygen,
distil off or sublime. Within the given temperature and pressure limits, those conditions are preferably chosen under which the compounds corresponding to the formula (I) wherein R and R¹ together are

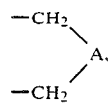

wherein
A represents the group

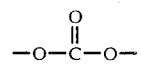

or oxygen,
sublime.

Whether spiro-bis-(dimethylene carbonate) (see formula (V)) and/or oxetane-3,3-dimethylene carbonate (see formula (VI)) are obtained as the reaction product depends on the presence or absence of catalysts in step (d) of the process according to the invention. In the absence of catalysts, or in the presence of weak catalysts, virtually exclusively spiro-bis-(dimethylene carbonate) is obtained, whilst in the presence of strong catalysts carbon dioxide is split off and virtually exclusively oxetane-3,3-dimethylene carbonate is obtained. Examples of weak catalysts are organic compounds of divalent or tetravalent tin, of tetravalent titanium or of zirconium, such as tin(II) dioctoate, tin(II) dilaurate, dibutyltin dilaurate, titanium tetrabutylate, titanium tetraisooctylate or titanium tetradodecylate. Weak catalysts can be employed in quantities of, for example, from 0.01 to 1% by weight, preferably from 0.01 to 0.1% by weight, relative to the quantity of polycarbonate. Compared to the procedure in the absence of catalysts, the addition of weak catalysts has the advantage that the transesterification leading to the formation of the spirobis-(dimethylene carbonate) is accelerated, whereby, in step (d), the reaction time can be reduced and/or the reaction temperature can be lowered.

Examples of stronger catalysts are those which can be employed in step (a), in the reaction of pentaerythritol with carbonates, that is to say, for example, oxides, hydroxides, alcoholates, carboxylates and carbonates of alkali metals, in particular sodium and potassium, and of aluminium, thallium or lead. Stronger catalysts can be employed in quantities of, for example, from 0.0001 to 0.5% by weight, preferably from 0.01 to 0.1% by weight, relative to the quantity of polycarbonate.

If, in step (d), the reaction is to be carried out in the presence of catalysts, the addition of the catalysts can be effected at various times during the course of the process. If stronger catalysts have already been employed in the reaction of pentaerythritol with carbonates in step (a), these catalysts can remain during the entire process. Weak catalysts and stronger catalysts can be added, for example, after step (b) and/or after step (c). If, in step (d), the reaction is to be carried out in the absence of catalysts, step (b) of the process cannot be dispensed with.

The carbonic acid derivatives which are collected in step (e) and are of the formula (I) wherein R and R¹ together are

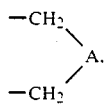

wherein
A represents the group

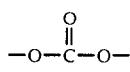

or oxygen,
are in general not yet completely pure. If desired, they can be purified, for example by recrystallization or sublimation. Dioxane, diethyl carbonate or ethyl acetate, for example, are suitable for the recrystallization of spiro-bis-(dimethylene carbonate) and ethyl acetate, for example, is suitable for the recrystallization of oxetane-3,3-dimethylene carbonate.

As mentioned above, step (d) of the process can be carried out in such a manner that virtually only one of the two compounds corresponding to the formulae (V) or (VI) is obtained in each case. However, if the catalysts and parameters given in the description of step (d) are not optimally maintained or selected, mixtures of the compounds corresponding to the formulae (V) and (VI) can also be collected in step (e). Such mixtures can be separated in a simple manner, since oxetane-3,3-dimethylene carbonate (see formula (VI)) is readily soluble in methylene chloride, but spiro-bis-(dimethylene carbonate) (see formula (V)) is virtually insoluble in methylene chloride.

In the preparation of the new carbonic acid derivatives of the formula (I)
wherein
R =

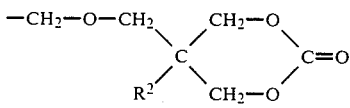

and $R^1$ and $R^2$ independently of one another are methyl or ethyl,
the process is preferably carried out such that di-trimethylolalkanes of the formula (XII)

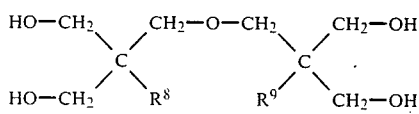 (XII)

in which
$R^8$ and $R^9$ can be identical or different and represent methyl or ethyl,
(a) are reacted with a carbonic acid derivative from the group comprising phosgene, chlorocarbonates, dialkyl carbonates and diaryl carbonates, to give a soluble precursor,
(b) if, in step (a), the reaction was carried out in the presence of a basic compound, these basic compounds are removed,
(c) the crosslinked polycarbonate is prepared from the soluble precursor, in the absence of catalysts or in the presence of weak transesterification catalysts, by heating to temperatures in the range of, preferably, from 150° to 240° C. and under pressures in the range of, preferably, from 0.001 to 10 mbars, and
(d) the crosslinked polycarbonate is depolymerized at temperatures of, preferably, from 240° to 320° C. and under pressures in the range of, preferably, from 0.001 to 2 mbars, and the bicyclic ether carbonate, which passes over, of the formula (I) wherein R =

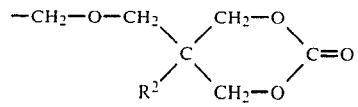

and $R^1$ and $R^2$ independently of one another are methyl or ethyl, is collected in a cooled receiver.

The di-trimethylolalkanes, for example di-(trimethylolethane) (formula XII, $R^8$ and $R^9$=methyl) or di-(trimethylolpropane) (formula XII, $R^8$ and $R^9$=ethyl), which are to be employed in the process according to the invention are by-products produced in the large-scale industrial production of trimethylolalkanes.

The reaction, to be carried out in step (a) of the process according to the invention, with one of the carbonic acid derivatives indicated can be carried out, in principle, using phosgene, chlorocarbonates, dialkyl carbonates or diaryl carbonates. For ecological reasons, the reaction using dialkyl carbonates or diaryl carbonates is preferred, for which reason essentially this procedure is described below. One skilled in the art will experience no difficulties in carrying out corresponding reactions using phosgene or chlorocarbonates.

The essential point in step (a) is that the reaction leads to a soluble product and not to an insoluble, strongly crosslinked polymer. This can be achieved, for example, by employing a large excess of dialkyl carbonate or diaryl carbonate, for example from 4 to 10 mols of carbonate per mol of a compound of the formula (XII).

The reaction with carbonates is preferably carried out in the presence of transesterification catalysts, in order to increase the rate of reaction. The following may be mentioned as examples of such transesterification catalysts: oxides, hydroxides, alcoholates, carboxylates and carbonates of alkali metals, in particular of sodium and/or potassium, and of aluminum, thallium or lead, which can be employed, for example, in quantities of from 0.2 to 4 g per mol of the compound of the formula (XII).

The reaction between carbonates and compounds of the formula (XII) can be carried out, for example, in such a manner that the components are mixed, one or more transesterification catalysts are added and the mixture is heated, for example to temperatures in the range of from 120° to 140° C., and the resulting alcohol is distilled off, if desired under reduced pressure and, if desired, over a column. When diethyl carbonate is employed as the carbonate, the reaction mixture can, for example, be boiled under reflux at a temperature of up to 130° C., and the resulting ethyl alcohol can be separated off over a column, at about 78° to 80° C.

If, instead of carbonates, the reaction is carried out using phosgene or chlorocarbonates, for example phenyl chlorocarbonate, the reaction is preferably carried out in the presence of a solvent, for example ethyl acetate, and an acid-binding agent, for example dimethylaniline, at temperatures of, for example, from 20° to 80° C. in a manner which is in principle known. In this case, after the reaction has ended, the solvent and the salt formed from the acid-binding agent have to be removed, for example by washing with water and stripping off the solvent under reduced pressure.

If basic compounds have been employed in step (a), for example as transesterification catalysts or as acid-binding agents, these compounds have to be removed in step (b). The removal of the basic compounds can be carried out in various ways. The procedure is preferably carried out, in this case also, as described in the preparation of carbonic acid derivatives of the formula (I) wherein $R=-CH_2OH$ and $R^1=C_1$- to $C_4$-alkyl.

In general, it is advantageous to remove as completely as possible, before carrying out step (c), the auxiliaries (for example water, acids, solvents and/or ion exchangers) used for the removal of the basic compounds. Ion exchangers can be removed, for example, by filtration or by using a suitable column, and solvents can be removed, for example, by stripping off under reduced pressure.

In step (c), a crosslinked polycarbonate is then prepared from the soluble precursor, freed from basic compounds, by heating the precursor to, preferably, from 150° to 240° C. under pressures in the range of, preferably, from 0.001 to 10 mbars. In this step, substances which are still present or are being formed and are more readily volatile than the compounds of the formula (I) wherein $R=$

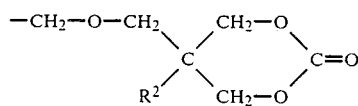

and $R^1$ and $R^2$ independently of one another are methyl or ethyl, can distil off, for example diethyl carbonate. After step (c) has been carried out, the crosslinked polycarbonate formed remains as the residue.

Step (c) of the process according to the invention is carried out in the absence of catalysts or in the presence of weak transesterification catalysts. Examples of weak transesterification catalysts are organic compounds of divalent or tetravalent tin or of tetravalent titanium, such as tin(II) dioctoate, tin(II) dilaurate, dibutyl-tin dilaurate, tin(II) diacetate, titanium tetrabutylate, titanium tetraisooctylate or titanium tetradodecylate. Such weak transesterification catalysts can be employed in quantities of, for example, from 0.001 to 0.5% by weight, preferably from 0.01 to 0.1% by weight, relative to the quantity of polycarbonates. Compared to the procedure in the absence of catalysts, the addition of weak transesterification catalysts has the advantage that higher yields of dicarbonates can be obtained.

In step (d), the crosslinked polycarbonate is depolymerized at temperatures in the range of, preferably, from 240° to 320° C., particularly preferably from 250° to 280° C., and under pressures in the range of, preferably, from 0.001 to 2 mbars, particularly preferably from 0.05 to 0.2 mbar. In this step, the compounds corresponding to the formula (I) wherein $R=$

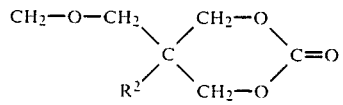

and $R^1$ and $R^2$ independently of one another are methyl or ethyl distil off or sublime. Within the given temperature and pressure limits, those conditions are preferably chosen under which the compounds corresponding to the formula (I) wherein $R=$

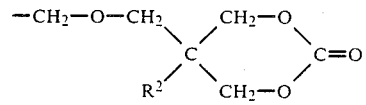

and $R^1$ and $R^2$ independently of one another are methyl or ethyl distil off. These compounds can also be made to pass over, or to pass over more readily, by passing, under the given conditions, an inert gas, such as nitrogen, carbon dioxide or a noble gas, through the vessel in which the depolymerization takes place.

The compounds passing over in step (d) can be collected in a cooled receiver. These compounds are then produced, in general, as a crystallizing mass. If desired, these compounds can be further purified, for example by recrystallization or repeated distillation. Toluene is an example of a suitable solvent for the recrystallization.

The preparation of the new carbonic acid derivatives of the formula (I) wherein $R=$

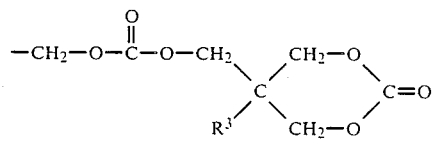

and $R^1$ and $R^3$ are each $C_1$- to $C_4$-alkyl, is preferably effected as described above for the preparation of the new carbonic acid derivatives of the formula (I) wherein $R=-CH_2OH$ and $R^1=C_1$- to $C_4$-alkyl, followed by the reaction of the resulting products with phosgene, in the presence of basic compounds, for example pyridine.

A carbonate of the formula (XIII)

(XIII)

wherein
  $R^{10}$ and $R^{11}$ can be identical or different and represent $C_1$- to $C_4$-alkyl or phenyl,
or wherein
  $R^{10}$ and $R^{11}$ together represent the group

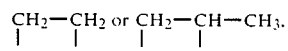

is preferably employed in the reaction, according to the invention, of a polyol of the formula (VII) using a carbonic acid derivative from the group comprising phosgene, chlorocarbonates, dialkyl carbonates and diaryl carbonates. For ecological reasons, diethyl carbonate is particularly preferably employed (formula (XIII), $R^{10}$ and $R^{11}$ are ethyl).

It is extremely surprising that it is possible, according to the invention, to prepare and to isolate the cyclic carbonates of the formula (I), since, according to J.A.C.S. 79, 3,455 (1957), the carbonate of trimethylolpropane already decomposes at 180° to 200° C., with decarboxylation and the formation of hydroxymethyloxetanes.

The present invention furthermore relates to the use of cyclic carbonic acid derivatives of the formula (I)

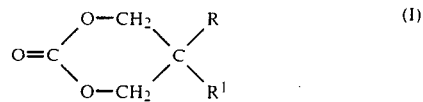

in which

R denotes either —CH$_2$OH, R$^1$ then representing an alkyl radical having 1 to 4 C atoms, or

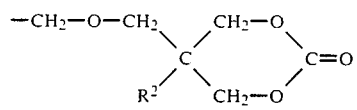

R$^1$ and R$^2$ then independently of one another representing methyl or ethyl, or

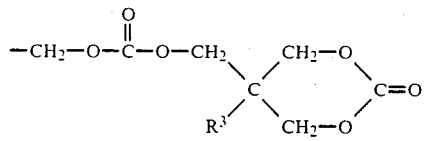

R$^1$ and R$^3$ then each representing an alkyl radical having 1 to 4 C atoms,
or in which
R and R$^1$ together denote

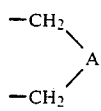

wherein
A represents the group

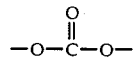

or oxygen,
as copolymerization components for the preparation of polycarbonates.

For example, an insoluble transparent polymer which cannot be melted is obtained from the compounds of the formula (I), if the latter are polymerised together with other organic carbonates, for example neopentyl glycol carbonate, using basic catalysts at an elevated temperature. Examples for suitable catalysts are oxides, hydroxides, alcoholates, carboxylates and carbonates of alkali metals, in particular sodium and potassium, and of aluminum, thallium or lead. Such catalysts can be employed in quantities of, for example, from 0.0001 to 0.5% by weight relative to to the organic carbonates. Suitable temperatures are, for example, those between 50° and 200° C., preferably 90° to 180° C. The polymerization can normally be carried out within 3 minutes to 10 hours. For a given polymerization the optimum reaction time depends mainly from the catalyst used and from the temperature applied.

Thus it is possible, for the first time, to prepare hot-hardening polycarbonates (duromers) by polymerization, that is to say without eliminating substances which form bubbles and which pollute the environment. In contrast to the known duromers based on unsaturated polyesters and styrene, the duromers obtainable according to the invention have a surprisingly high notched impact strength, so that, in general, they are not required to be reinforced with glass fibres.

The insoluble transparent polymers which can be obtained from compounds of the formula (I) when polymerized together with other organic carbonates, preferably neopentyl glycol carbonate, have outstanding chemical, physical and electrical properties, especially a small phase angle, a high tracking resistance, a high resistance to chemical and electrolytical corrosion, a high resistance to saponification, a good transparency, a high resistance to yellowing and a high resistance to oil and gasoline. The polymers obtainable in this way can therefore be used for the production of different products requiring such properties, for example, for the production of electrical equipment such as lighting equipments, lighting fixtures, protective supports for lamps, plug boards, cable reels and distribution boxes, for the production of constructional units such as light-permeable roof domes, light permeable sheets, roof sheetings, panellings, constructional units for green houses and sanitary installations and for the production of constructional parts for motor vehicles and boats, such as safety windscreens and shaped or moulded parts.

EXAMPLES

EXAMPLE 1

268 g (2 mols) of trimethylolpropane, 236 g (2 mols) of diethyl carbonate and 1 g of potassium carbonate were heated under reflux, whilst stirring, in a 1 m packed column, whilst ethanol was distilled off, at 78° C., via the top until the internal temperature had risen to 130° C. and 86 g of ethanol were separated off. By gradually reducing the pressure to 30 mbars, the remaining quantity of ethanol was distilled off, amounting to 164 g (=4 mols) in total. The reaction product, a resin which scarcely flows at room temperature, was dissolved in 700 ml of methylene chloride/dioxane (1:1) and was allowed to run over an ion exchanger, namely a bead polymer of sulphonated, crosslinked polystyrene. The solvent was removed under reduced pressure and 312 g of residue was obtained. By means of a dropping funnel heated to 155° C., the crude product was distilled from a stirred flask, pre-heated to 220° C., in the course of 100 minutes at 170° C., under a pressure of 0.02 mbar. A cold trap cooled with methanol/dry ice and a cold trap cooled with liquid nitrogen were used for this purpose. 292 g (91% of theory) of colourless distillate which crystallized at room temperature were obtained. The melting point was from 31° to 32° C. After recrystallization from diethyl ether, the melting point was from 40° to 41° C.

Elementary analysis: C$_7$H$_{12}$O$_4$ (160.1) C calculated: 52.51; found: 52.68; H calculated: 7.56; found: 7.41; O calculated: 39.98; found: 39.67

The product was trimethylolpropane monocarbonate (see formula II), which was characterized as the phenylurethane of melting point 112° C. (from toluene).

EXAMPLE 2

10.5 g (0.106 mol) of phosgene was passed into a solution of 32 g (0.2 mol) of trimethylolpropane monocarbonate, which was obtained according to Example 1, in 50 g of pyridine at room temperature, and the mixture was kept at 60° C. for 1 hour. The mixture was then diluted with methylene chloride, the excess pyridine was extracted by shaking with 2N hydrochloric acid, the residual solution was dried over sodium sulphate and the solvent was removed under reduced pressure. 30.2 g of a residue of melting point 248° to 254° C. were obtained (recrystallized from ethyl acetate). The compound is di-(trimethylolpropane carbonate) carbonate of the following formula (IV)

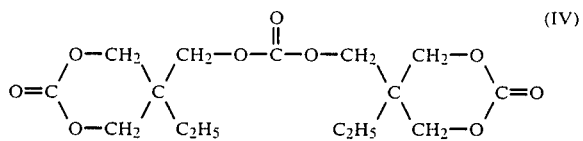

Elementary analysis: $C_{15}H_{22}O_9$ (346.3) C calculated: 52.02; found: 52.31; H calculated: 6.41; found: 6.28; O calculated: 41.58; found: 41.30

EXAMPLE 3

9 g of neopentyl glycol carbonate, 1 g of di-(trimethylolpropane carbonate) carbonate, which was obtained according to Example 2, and 0.1 g of ground potassium carbonate were heated to 130° C. Polymerization occurred, with an increase in temperature, to give an opaque reaction product which could not be melted, was insoluble in solvents, and had great toughness, resilience and strength.

EXAMPLE 4

240 g (2 mols) of trimethylolethane, 260 g (2.2 mols) of diethyl carbonate and 1 g of sodium methylate were reacted in a 1 m packed column, whilst stirring, in the same manner as in Example 1. After 2 hours 45 minutes, 185 g of ethanol had been separated off. The residue, a viscous resin, was dissolved in 600 ml of methylene chloride and the solution was allowed to run over an ion exchanger, namely a sulphonated crosslinked polystyrene. The solvent was removed under reduced pressure and 286 g of residue were obtained. 40 g of this residue were distilled from a Claisen flask, whilst stirring, at an internal temperature of 210° C. and a pass-over temperature of from 160° to 180° C. 32 g of a crystallized distillate of melting point from 93° to 94° C. were obtained (recrystallized from ether). This compound is trimethylolethane monocarbonate (see formula II).

Elementary analysis: $C_6H_{10}O_4$ (146.1) C calculated: 49.32; found: 49.28; H calculated: 6.90; found: 6.98; O calculated: 43.81 found: 43.62

EXAMPLE 5

136 g (1 mol) of pentaerythritol, 708 g (6 mols) of diethyl carbonate, 100 mg of thallium carbonate and 200 mg of lead naphthenate were heated under reflux (126°–128° C.) in a 90 cm packed column, whilst ethyl alcohol was taken off at the top of the column, at 78° to 80° C. After a reaction time of 14 hours, the calculated quantity of ethyl alcohol had been separated off (184 g = 4 mols). 70 g of the residue, a slightly cloudy colourless liquid (628 g), were heated to 200° C. in the course of 3 hours, under a pressure of 20 mbars, in a wide-necked flask which was part of a sublimation apparatus, in order to separate off the excess diethyl carbonate (48 g). The residual viscous resin (25 g) was then kept at a sublimation temperature of from 200° to 230° C., under a pressure of from 0.03 to 0.05 mbar. After every 1.5 hours, the sublimate was scraped off. In a period of 10 hours, 11 g of sublimate of melting point 110° to 122° C. were obtained. After recrystallization from ethyl acetate, 8 g of colourless crystals of melting point 135° to 136° C. were obtained. This compound was oxethane-3,3-dimethylene carbonate of the formula (VI)

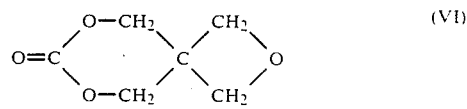

Elementary analysis: $C_6H_8O_4$ (144.1) C calculated: 50.00; found: 49.78; H calculated: 5.99; found: 5.49; O calculated: 44.40; found: 44.63

The $^1$H-NMR spectrum showed only one signal at 4.65 ppm, measured with respect to TMS ($\delta = 0$ ppm) as the standard.

The $^{13}$C-NMR analysis indicated four different types of C atoms.

In the IR spectrum, the CO band at 1,740 cm$^{-1}$ and the band at 980 cm$^{-1}$ for the oxetane ring are characteristic.

The substance reacts with ethereal hydrochloric acid with evolution of heat.

EXAMPLE 6

340 g (2.5 mols) of pentaerythritol, 1,770 g (15 mols) of diethyl carbonate and 2.5 g of thallium carbonate were heated under reflux in a 1 m packed column, whilst ethanol was taken off at the top of the column, at 78° to 80° C. After 4 hours, 475 g of distillate had been separated off. The reaction product was taken up with methylene chloride and was extracted by shaking with 10 ml of 2N hydrochloric acid and with twice 200 ml of water, in order to remove the catalyst. After the solution had been dried over sodium sulphate, it was concentrated and freed from excess diethyl carbonate under reduced pressure at 150° C./14 mbars. The residue was 819 g. 50 mg of tin dilaurate were added to 150 g of this residue in a pear-shaped flask, and the mixture was heated in a rotary evaporator from a bath temperature of 210° to 240° C. in the course of 1 hour, under a pressure of 1 mbar, until a crosslinked polycondensate was formed. 42 g of a crystalline substance was sublimed from the pear-shaped flask. which was part of a sublimation apparatus, in the course of 12 hours at 220° to 250° C. and 0.03 mbar; this substance was spiro-bis-(dimethylene carbonate) of the formula (V)

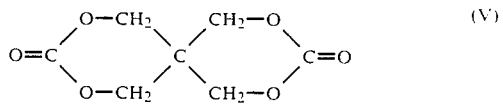

The melting point of this substance was from 222° to 228° C. (evolution of gas). The substance proved to be virtually insoluble in methylene chloride and can be recrystallized from dioxane or diethyl carbonate.

Elementary analysis: C₇H₈O₆ (118.1) C calculated: 44.69; found: 44.31; H calculated: 4.28; found: 4.38; O calculated: 51.03; found: 50.91

The ¹H-NMR spectrum showed only a single signal at 4.65 ppm, and the IR spectrum showed a CO band at 1.741 cm⁻¹.

The band, at 980 cm⁻¹, which is typical for an oxetane, is missing. No evolution of heat takes place with ethereal hydrochloric acid.

EXAMPLE 7

9 g of neopentyl glycol carbonate, 1 g of spiro-bis-(dimethylene carbonate) (obtained according to Example 6) and 0.01 g of ground potassium carbonate were heated to 130° C. Polymerization occurred, with a sudden increase in temperature to 150° C., to give a transparent polymer which could not be melted and which was insoluble in solvents. This polymer is distinguished by great hardness and high notched impact strength and resilience.

EXAMPLE 8

78.3 g (0.5 mol) of phenyl chlorocarbonate were allowed to run dropwise, whilst stirring, into a suspension of 34 g (0.25 mol) of finely ground pentaerythritol, 200 ml of dried ethyl acetate and 60.5 g (0.5 mol) of dimethylaniline, and the mixture was warmed to 60° C. for half an hour. After the mixture had cooled, it was twice extracted by shaking with water, the organic phase was dried over sodium sulphate, and the solvent was removed under reduced pressure. The residue (65 g) essentially consisted of pentaerythritol bisphenyl carbonate. It was heated to from 150° to 200° C. at 17 mbars, until phenol had been completely split off (31 g). 10 g of the residue were heated in a sublimation apparatus to 230° C. at 0.02 mbar. 1 g of crystals of melting point 220° to 230° C. (evolution of gas) were obtained; these crystals were spiro-bis-(dimethylene carbonate) (see formula V).

EXAMPLE 9

134 g (1 mol) of pentaerythritol, 710 g (6 mols) of diethyl carbonate, 100 mg of thallium carbonate and 200 mg of lead naphthenate were heated under reflux (125°–130° C.) in a 1 m packed column, whilst ethanol was distilled off via the top, at 78° to 80° C. After 18.5 hours, 183 g of ethanol had passed over. The residue (640 g) was stirred for 1 hour at 100° C. with 20 g of commercial acid-activated bleaching earth. The solid constituents were separated off using a pressure filter, and the filtrate was heated up to an internal temperature of 150° C. under a pressure of 20 mbars and thereby freed from excess diethyl carbonate (326 g). By distilling the residue in a high vacuum at 190° to 192° C. and 0.07 mbar, 255 g of a colourless viscous liquid were obtained. This liquid was dissolved in toluene and when the solution was cooled 86 g of crystals of melting point 91° to 92° C. were precipitated. This compound was pentaerythritol monocarbonate bis-ethyl carbonate (see formula (XIV)). The concentrated mother liquor was triturated with methanol and 153 g of crystals of melting point 55° to 57° C. were obtained. This compound was pentaerythritol tetrakis-ethyl carbonate (see formula XV).

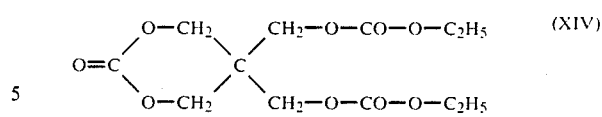

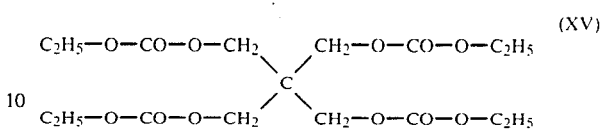

Bicyclic pentaerythritol carbonates were prepared from these two derivatives of pentaerythritol by sublimation under reduced pressure, as follows:

(a) 2 g of pentaerythritol monocarbonate bis-ethyl carbonate (XIV) were heated with 2 mg of dibutyl-tin dilaurate to 220° C. Approx. 7 g of diethyl carbonate distilled into the receiver. The residue was cross-linked. It was heated in a sublimation apparatus to 220° to 260° C. at 0.03 mbar. 0.63 g of crystals of melting point 210° to 230° C. (evolution of gas) was obtained from the sublimate. This compound was spiro-bis-(dimethylene carbonate) (see formula V).

(b) 4 g of pentaerythritol tetrakis-ethyl carbonate (XV) were heated with 2 mg of tin dilaurate to 180° to 220° C. 2 g of diethyl carbonate collected in the receiver. The crosslinked residue was heated in a sublimation apparatus to 220° to 250° C. at 0.02 mbar. The crystalline sublimate was recrystallized from ethyl acetate. 0.8 g of crystals of melting point 220° to 230° C. (evolution of gas) was obtained. This compound was spiro-bis-(dimethylene carbonate) (see formula V).

EXAMPLE 10

20 g of the crude product obtained according to Example 6 after removal of the catalyst were mixed with 10 mg of sodium hydroxide, dissolved in methanol, and the mixture was heated to 200° C. at 20 mbars, 1.3 g of diethyl carbonate passing over. Heating was continued at 220° to 240° C. and under 0.05 mbar, and a distillate which passes over at 150° to 180° C. and which predominantly solidifies to crystals is obtained (4.5 g). After recrystallization from ethyl acetate, the melting point was 128° to 130° C. The compound was oxetane-3,3-dimethylene carbonate (see formula VI).

EXAMPLE 11

125 g (0.5 mol) of di-(trimethylolpropane), 295 g (2.5 mols) of diethyl carbonate and 0.5 g of ground potassium carbonate were heated under reflux in a 1 m packed column, whilst ethanol distilled off via the top, at 78° C. After 2.5 hours, 90 g of ethanol had been separated off. The bottom temperature did not exceed 130° C. in this process. The reaction product was taken up in 600 ml of methylene chloride and the solution thus obtained was introduced through a tube charged with 200 g of an ion exchanger consisting of a sulphonated crosslinked polystyrene. 211 g of residue were obtained after concentration of the solution at temperatures of up to 90° C. and under 15 mbars.

After the addition of 100 mg of tin dilaurate whilst stirring, 86 g of this residue were heated from 160° to 230° C. under 0.01 mbar, in the course of one hour. The highly crosslinked polycarbonate present shortly thereafter was brought to temperatures of from 260° to 290° C. under 0.01 mbar, the polycarbonate again becoming liquid in the intervening period, whilst 60 g of viscous distillate which crystallizes when cold passed over at 250° to 265° C. 24 g of diethyl carbonate were collected in a cold trap charged with dry ice and located downstream from the collecting vessel for the distillate, and 1 g of carbon dioxide was collected in a further cold trap cooled with liquid nitrogen. The distillate obtained was recrystallized from 250 ml of toluene. The compound was di-(trimethylolpropane) dicarbonate of the formula (III) and was obtained in a yield of 49 g, corresponding to 79% of theory. After recrystallization, the melting point was 102° to 103° C.

Elementary analysis: $C_{14}H_{22}O_7$ (302.3) C calculated: 55.62 found: 55.33 H calculated: 7.34 found: 7.51 O calculated: 37.05 found: 37.30

EXAMPLE 12

9 g of neopentyl glycol carbonate, 1 g of di-(trimethylolpropane) dicarbonate (obtained according to Example 11) and 0.1 g of potassium carbonate were heated to 130° C. Polymerization occurred, with an increase in temperature, to give a transparent polymer which could not be melted, was insoluble in solvents, and had a high viscosity and great hardness and resilience.

In a bending test according to DIN 53452 (German Industrial Standard No. 53452) following characteristics were determined:

Flexural strength: 125 MPa
Bending under load: 11 mm
Edge fibre elongation: 6.2%
E-modulus [MPa]: 2800

EXAMPLE 13

The procedure was carried out as in Example 11, up to and including the treatment with the ion exchanger and the concentration of the solution, 90 g of the residue thus obtained were heated to 180° to 220° C. for 1.5 hours, without the addition of a catalyst. During this process, 26 g of diethyl carbonate collected in the receiver charged with dry ice. The actual reaction product was distilled off at an internal temperature of from 250° to 295° C. and a distillation temperature of from 260° to 280° C., under 0.01 mbar. 62 g of a mass which crystallizes were obtained and were recrystallized from toluene, whereupon 48 g of crystals of melting point 100° to 102° C. were produced. The yield was 74% of theory. The same compound was obtained as in Example 11.

EXAMPLE 14

This example illustrates the use of copolymerisates of neopentyl glycol carbonate and di-(trimethylolpropane)-dicarbonate in the production of safety windscreens.

A melt consisting of 9 parts by weight of neopentyl glycol carbonate, 1 part by weight of di-(trimethylolpropane)-dicarbonate and 0.0001 parts by weight of thallium isooctoate was poured between two glass sheets wiped with silicone oil and kept at 120° C. for 20 minutes.

The glass sheets held together by the colourless transparent copolymer formed from the poured in melt cannot be separated from each other and adhere to the copolymer without producing glass splinters when they are broken by force.

What is claimed is:

1. A cyclic carbonic acid compound of the formula

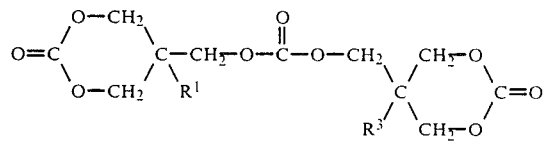

wherein $R^1$ and $R^3$ are independently methyl or ethyl.

2. A cyclic carbonic acid compound according to claim 1, which is di-(trimethylolpropane carbonate) carbonate of the formula

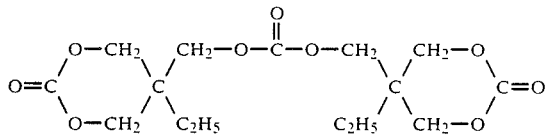

* * * * *